(12) United States Patent
Declerck et al.

(10) Patent No.: US 8,693,741 B2
(45) Date of Patent: Apr. 8, 2014

(54) METHODS AND APPARATUS FOR ANALYZING MEDICAL IMAGING DATA (75) Inventors: Jerome Declerck, Oxford (GB); Timor Kadir, Oxford (GB); Matthew David Kelly, Botley (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 869 days.

(21) Appl. No.: 12/575,653

(22) Filed: Oct. 8, 2009

(65) Prior Publication Data

US 2010/0092052 A1   Apr. 15, 2010

(30) Foreign Application Priority Data

Oct. 9, 2008 (GB) .................................. 0818494.7
Oct. 9, 2008 (GB) .................................. 0818495.4

(51) Int. Cl.
*G06K 9/00* (2006.01)
*G06K 9/62* (2006.01)

(52) U.S. Cl.
USPC .......................................... 382/128; 382/100

(58) Field of Classification Search
USPC ......................................................... 382/128
See application file for complete search history.

(56) References Cited

U.S. PATENT DOCUMENTS

| 5,165,100 A | 11/1992 | Hsieh et al. |
| 5,841,832 A | 11/1998 | Mazess et al. |
| 6,353,803 B1 | 3/2002 | Degani |
| 6,490,476 B1 * | 12/2002 | Townsend et al. ............ 600/427 |
| 7,176,466 B2 | 2/2007 | Rousso et al. |
| 2004/0081270 A1 | 4/2004 | Heuscher |
| 2005/0020900 A1 | 1/2005 | Yngvesson et al. |
| 2007/0160276 A1 | 7/2007 | Chen et al. |
| 2007/0237372 A1 | 10/2007 | Chen et al. |
| 2009/0018438 A1 | 1/2009 | Schroder et al. |

FOREIGN PATENT DOCUMENTS

| SU | 957862 | 9/1982 |
| SU | 988278 | 1/1983 |
| SU | 1142101 | 2/1985 |
| UA | 76 050 C2 | 12/2004 |
| WO | WO 2009/150565 | 12/2009 |

OTHER PUBLICATIONS

Yagle, Evaluation of (18)F-Annexin V as a PET Imaging Agent in an Animal Model of Apoptosis, J Nucl Med 2005; 46:658-666.*
Beaulieu, SUV varies with time after injection in (18)F-FDG PET of breast cancer: characterization and method to adjust for time differences, J Nucl Med 2003; 44:1044-1050.*
"Spatiotemporal Reconstruction of List-Mode PET Data," Nichols et al, IEEE Trans. on Medical Imaging, vol. 21, No. 4 (2002) pp. 396-404.

* cited by examiner

*Primary Examiner* — Tran Nguyen
(74) *Attorney, Agent, or Firm* — Schiff Hardin LLP (57) ABSTRACT

In a method and apparatus for analyzing medical imaging data of a subject from an imaging modality using a tracer, data from detection of tracer emission events at least one region of a scanned imaging volume are obtained, and the data processed to establish sub-periods or time points within a scan period for the emission events. A rate of change of emission events per unit time for a given region is then calculated, for example by obtaining a number of emission events in each sub-period in the given region, and fitting a line through the values for the sub-periods.

13 Claims, 8 Drawing Sheets

METHODS AND APPARATUS FOR ANALYZING MEDICAL IMAGING DATA

BACKGROUND OF THE INVENTION

1. Field of the Invention

This invention concerns methods and apparatuses for analyzing medical imaging data of a subject from an imaging modality using a tracer.

2. Description of the Prior Art

In the medical imaging field, several nuclear medicine emission imaging schemes are known. For example PET (Positron Emission Tomography) is a method for imaging a subject in 3D using an ingested radio-active substance which is processed in the body, typically resulting in an image indicating one or more biological functions. FDG, for instance, is a glucose analog which is used as the radiopharmaceutical tracer in PET imaging to show a map of glucose metabolism. For cancer, for example, FDG is particularly indicated as most tumors are hypermetabolic, which will appear as a high intensity signal in the PET image. For this reason, PET imaging is widely used to detect and stage a wide variety of cancers. The level of glucose activity is usually highly correlated with the aggressiveness and extent of the cancer, and, for example, a reduction in FDG signal between a baseline and a follow-up scan is often indicative of a positive response to therapy.

A key criterion used in evaluating suspicious lesions in a PET scan is the Standardized Uptake Value (SUV). This value is computed from the number of counts of emission events recorded per voxel in the image reconstructed from the event data captured in the PET scan (coincidence emission events along the line of response). The SUV value can also, for example, be adjusted with the intention of accounting for differences in body mass/composition and concentration of radiotracer injected. Effectively the SUV's purpose is to provide a standardized measure of the spatial distribution of radiotracer concentration throughout the imaged portion of the body.

The concentration of radiotracer accumulating in any given tissue region in the body is dependent upon both the affinity of that tissue region for the tracer and the supply of tracer to that tissue region.

Conventionally, PET scans are acquired using a static protocol, producing a single image volume representing the average counts (per voxel) detected over a fixed, short period of time following a given interval between radiotracer injection and image acquisition. This is in contrast to a dynamic protocol, where data is acquired from the time of injection of the tracer, over a much longer period, (e.g. two hours).

Figure 1:
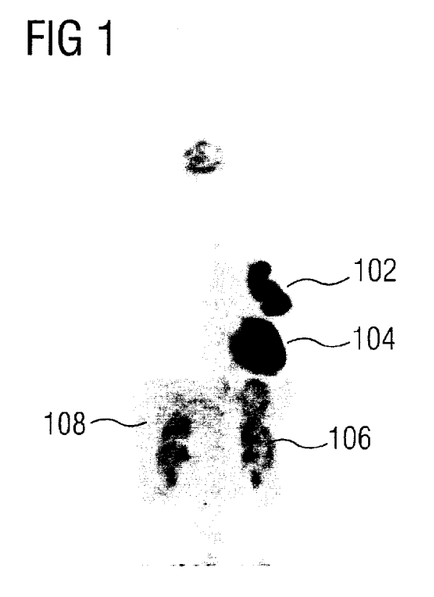
FIG. 1 is an example of an FDG PET image of a lung cancer patient.

It can be difficult in FDG PET imaging to differentiate various levels of glucose metabolism based solely on intensity in a static image. FIG. 1 is an image of a lung cancer patient imaged with FDG PET, where areas of high metabolism are shown in dark. It is expected to find in the body areas of normally high metabolism, for example, the liver (108), heart (104), brain, kidneys (106), and sometimes identification of malignancies (102) in these areas can be very challenging.

Moreover, even if normal high metabolism can be differentiated thanks to a sophisticated knowledge of anatomy and function of each organ, FDG PET can also show high uptake in regions of inflammation. Cellular mediators of inflammation (e.g., mononuclear cells such as monocytes and lymphocytes), along with malignant cells, also have elevated glucose, and therefore FDG, uptake.

Figure 2:
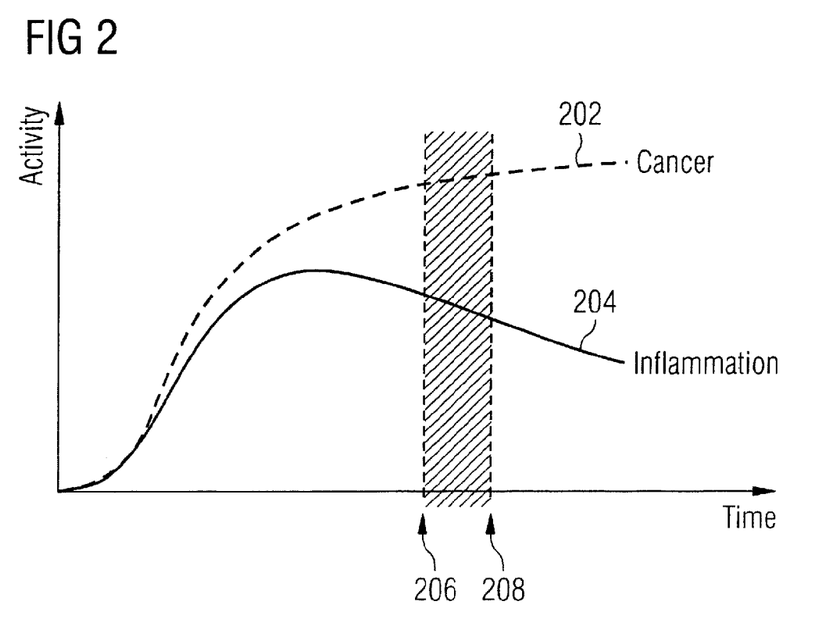
FIGS. 2 and 3 are schematic illustrations of time activity curves for cancer cells and inflamed cells in FDG PET scans.

Differentiation of malignancy from inflammation is therefore very difficult. It is known that over the first two hours after the injection of FDG, malignant cells will continue to take up FDG whereas inflamed cells will take up FDG and then wash it out progressively (or at least plateau). In FIG. 2, these time-activity curves represent schematically the different uptake patterns over time of FDG in cancer cells (202) and inflamed cells (204). The two dashed lines represent the beginning (206) and end (208) of a putative scanning time (static scan periods are typically between 1 and 10 minutes, depending on the acquisition protocol); the textured pattern in between the two represents the time during which data would be acquired to generate an image.

An image could be acquired so that most of the wash out has occurred, within reasonable time limits. However, in clinical routine, it is not easy to wait for too long a time, because:

a. the decay of the radioactive label forces the image acquisition to be made reasonably soon after the injection so that the image is not too noisy b. the longer the time the patient has to wait, the longer a room needs to be setup for the patient, which can cause some difficulty in the hospital logistics.

Figure 3:
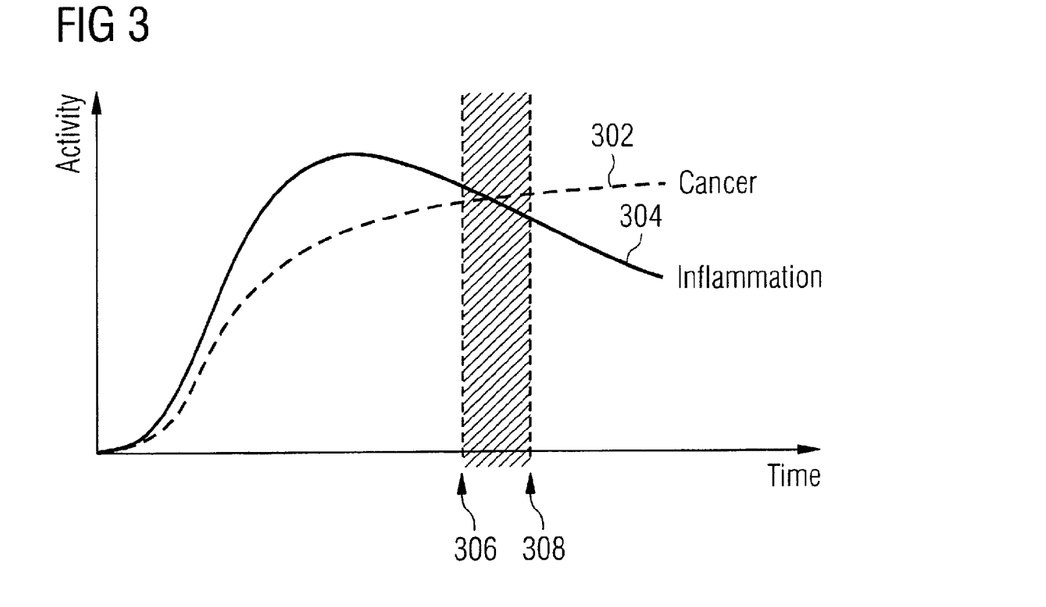

For these reasons, the image is usually acquired after 30 or 45 minutes, which is not long enough for the wash out to have completely happened. Therefore, the inflammation signal can still be present. Moreover, it may not in any case be possible to differentiate, from a single scan, inflammation from cancer as the relative level of uptake can be similar, depending on the patho-physiological conditions of the patient. FIG. 3 is a schematic illustration of a consequence of such imaging before wash out of tracer from inflammation. Again, the two dashed lines represent the beginning (306) and end (308) of the scanning time and the textured pattern in between represents the time during which data is acquired to generate an image. In this situation, intensity alone (i.e., mean activity measured during acquisition) would not allow differentiation of cancer (302) from inflammation (304), as the two tissues types are in this case at similar activity levels during the acquisition period.

Two protocols have been considered in order to differentiate these tissue types:

1) Dynamic protocol: a scan is acquired from injection of the tracer until long enough for the wash out of inflammation to start: pharmaco-kinetic analysis or clustering techniques can then be applied to differentiate the inflammation from the cancer. However, these scans can take a long time (e.g. two hours) and are not usually acceptable to perform in a clinical routine environment.

Figure 4:
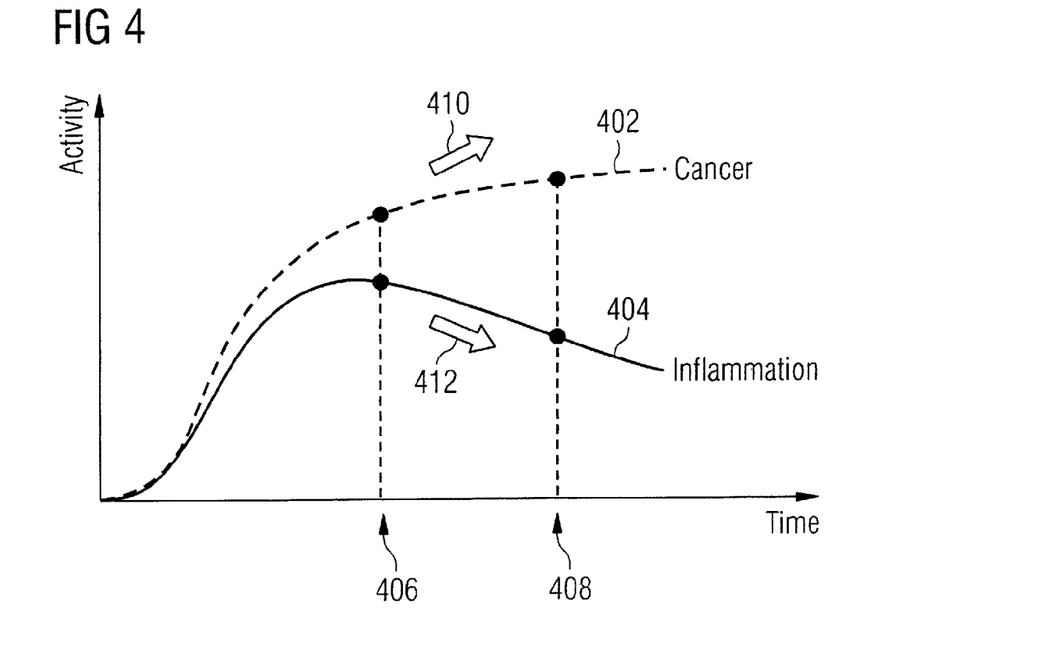
FIG. 4 is a schematic illustration of time activity curves in a dual time point FDG PET scan.

2) Dual time point scan (see FIG. 4): two scans are obtained at different time points (406, 408), after, say 60 and 90 minutes. If the uptake goes down between the time points (412), then it is assumed to be inflammation; if it goes up or stay stable (410), it is assumed to be cancer. These kind of protocols are also time consuming and not usually acceptable in a clinical environment.

SUMMARY OF THE INVENTION

An object of the present invention is to address these problems and provide improvements upon the known devices and methods.

In general terms, in an embodiment of the invention, a method of analyzing medical imaging data of a subject from an imaging modality using a tracer, includes obtaining data from detection of tracer emission events at least one region of a scanned imaging volume, processing the data to establish sub-periods within a scan period for the emission events, and calculating a rate of change of emission events per unit time for a given region.

This allows rate of change of uptake of a tracer to be measured for a short scan period, simply using the data already captured by the scan.

Preferably, the scan period over which the medical imaging data is obtained is a period of a static scan protocol. This means that that the data is obtained over the 'time period' of a typical static scan protocol (rather than that the storage of counts is performed only for a single sinogram).

The method can further include comparing the rate of change of emission events per unit time for the given region with an expected behavior for a particular type of tissue of a scan subject. Thus the type of tissue in the given region can be determined.

More preferably, the at least one region comprises a voxel of the imaging volume.

In an embodiment, the sub-periods are a number of divisions of the scan period, and wherein the step of processing then includes establishing a division for each emission event in the region within the scan period, and the step of calculating includes deriving a tracer uptake value for each division by obtaining a number of emission events in each division, fitting a line through the uptake values for the divisions, and using the slope of the fitted line to determine the rate of change of emission events per unit time for the given region.

This re-sampling is a simple method of determining the required rate of change.

In another embodiment, the sub-periods are time points within the scan period. The step of calculating then includes fitting a line through the emission events at the associated time points, and using a slope of the fitted line to determine the rate of change of emission events per unit time for the given region. This is an alternative method of determining the required rate of change, directly from the list-mode data.

Preferably, the method further includes generating a first representation of the medical imaging data from the calculated rate of change of emission events per unit time for the given region.

More preferably, the method further includes generating a second representation of data by obtaining data from detection of tracer emission events at the least one region of a scanned imaging volume, and averaging a number of emission events across the scan period for the given region.

This allows comparison of the standard representation of the data with the value for the rate of change of emission events (uptake) for the given region.

In another embodiment, wherein a first organ of the subject is of a type known to affect processing of the tracer in the subject, and a second organ of the subject is of a type known to accumulate the tracer as a function of an effect caused by the first organ, the method further includes obtaining data from detection of tracer emission events in a region of interest of the imaging volume representing the second organ, and comparing a rate of change of emission events per unit time for the region of interest, with a model for the rate of change of emission events per unit time for the second organ as a function of a normal effect due to the first organ.

Thus the rate of change of uptake can be used to evaluate the tracer uptake in the second organ.

Suitably, the first organ is the kidney, and the second organ is the bladder.

In another embodiment of the invention a method of analyzing medical imaging data of a subject captured by a medical imaging apparatus in an imaging modality using a tracer, includes obtaining, through a processor, data from detection of tracer emission events captured by the imaging apparatus at least one region of a scanned imaging volume, processing, in a processor, the data to establish sub-periods within a scan period for the emission events, calculating, in a processor, a rate of change of emission events per unit time for a given region, and displaying a value for the rate of change on a display device.

Preferably, the method further includes displaying the value together with an image of the subject generated from the imaging data.

In a further embodiment of the invention, an apparatus for analyzing medical imaging data of a subject captured by a medical imaging apparatus in an imaging modality using a tracer has a processor that obtains data from detection of tracer emission events captured by the imaging apparatus at least one region of a scanned imaging volume, process the data to establish sub-periods within a scan period for the emission events, and calculates a rate of change of emission events per unit time for a given region, and a display device that displays a value for the rate of change.

The invention also encompasses a computer-readable medium encoded with computer program codes that when the medium is loaded into or run on a computer, causes the computer to implement a method according to the embodiments described above.

BRIEF DESCRIPTION OF THE DRAWINGS

FIG. 6a is a diagram of a synthetic phantom used for calculation of a derivative of time activity curves for a PET scan according to an embodiment of the invention.

FIG. 6b is a graph illustrating time activity curves assigned to the phantom of FIG. 6a.

DESCRIPTION OF THE PREFERRED EMBODIMENTS

Figure 5:
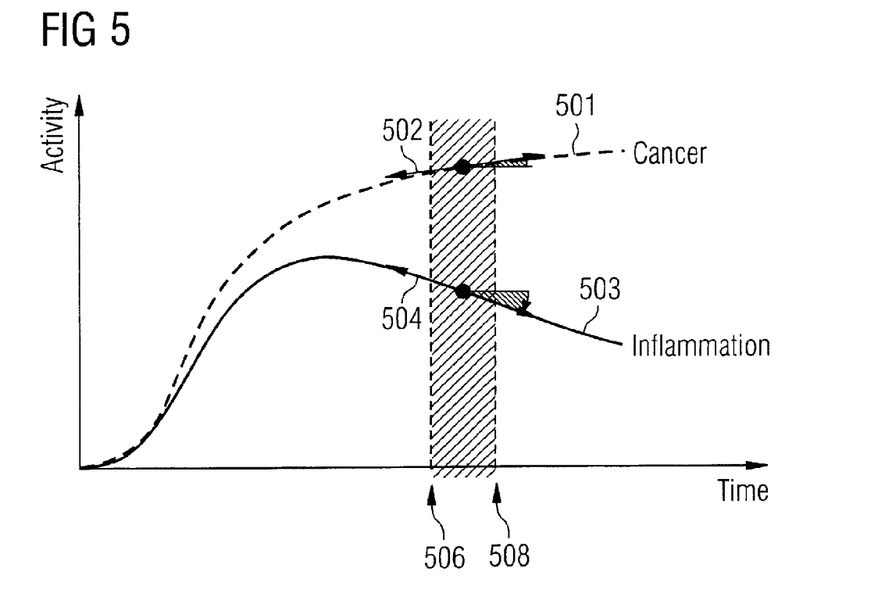
FIG. 5 is a schematic illustration of the calculation of derivatives of time activity curves for an FDG PET scan according to an embodiment of the invention.

When the following terms are used herein, the accompanying definitions can be applied:
PET—Positron Emission Tomography
ROI—Region of Interest
VOI—Volume (Region) of Interest
FDG—2-18F-Fluoro-2-deoxy-D-glucose
AUC—Area Under the Curve
SUV—Standardized Uptake Value
TAC—Time-Activity Curve In an embodiment of the invention, the method essentially computes a derivative image which allows calculation of the change of uptake over time. With reference to FIG. 5, the acquisition scan is taken between time points 506 and 508, and curves 501 and 503 are the TACs for two different tissue areas. Conventional image processing would usually measure the average of uptake over the scan time period (i.e. a flat line across the scan period 506 to 508). In this methodology, the derivative slopes 502 and 504 for the change of uptake over the acquisition period are derived.

The differing slopes can then be used to identify the different tissues types as cancerous and inflamed. If the rate of uptake is increasing, as in cancer (as shown in FIG. 5), the derivative image should have a positive signal. Otherwise, if the rate is decreasing, as for inflammation, the signal would be negative. Differentiation between malignancy and inflammation, or other non-malignant tissues with high uptake, may therefore be facilitated. It may be noted that, with reference to FIG. 5, if the acquisition scan were instead taken too soon after injection, the two tissue types would have similar, positive gradients, and thus differentiation would be more difficult.

A simple method of calculating this derivative is, rather than averaging an uptake value across the entire short scan period, to compute a series of images from the same list-mode data by resampling time in small intervals: for instance, from a 10 minute list-mode scan, 10 1-minute images can be reconstructed (or 5 2-minutes images, etc). From these 10 1-minute divisions, the 10 values of the signal at a specific point or region are taken, i.e. for each of the 10 divisions the uptake value, derived from the count of emission events at the given region or voxel, is measured. The 10 results or values can then be fitted with a line, and the slope of the line is therefore an estimate of the derivative at that region or voxel. The ratio computed by the two time point method described above can be compared to this fitting method, where only two points are used to fit the line.

The derivative values can be determined for each voxel or region (or indeed the entire image) and then, for example, displayed as an image in their own right, or the derivative values can be used for information in another image, for example as an overlay, or for use in further processing of the image data (for example, in the measurement of tracer clearance, described later).

The below alternative method using direct reconstruction may take better account of the noise by doing the fitting directly in the reconstruction.

The slope can also be calculated using list-mode data (i.e. the list of coincidence events) and a reconstruction algorithm which measures the rate of uptake. Methods like Nicholls (Nicholls et al. Spatial reconstruction of list-mode PET data, IEEE Trans Med Im 2002), which compute a spline function or an exponential model directly from list-mode can be adapted to estimate the slope directly in this manner. Such methods can be adapted by replacing the function used to fit the list mode events with a linear one i.e. a line specified by two parameters. In this case the algorithm may optimize both the slope and average uptake over the period of the scan. Such a reconstruction algorithm can be adapted to produce a conventional static image in addition to the slope or derivative image. In addition the Nicholls method requires the specification of so-called knot positions at which the spline basis functions are placed. In the present adapted version, the linear basis function is placed at the middle of the time period of the scan. Finally, the method can be adapted in a manner to estimate the slope in a VOI, not just in one voxel.

In addition to modifying the reconstruction software, reading workstations may also be modified in order to take advantage of the slope/derivative information. For example, the reading workstation may be able to load the additional information and to allow the user to make VOI calculations and comparisons. For example, the workstation may present both the usual average image, and also the slope information to the user for any VOI drawn by the user. Alternatively, the system may only indicate whether the uptake is likely to be increasing, stationary or decreasing instead of the actual calculate slope.

In an alternative embodiment, two or more time points are acquired for the same region within a single acquisition by making multiple passes over the body of the patient (i.e., the positions for head, chest, abdomen, pelvis, then again head, chest, abdomen, pelvis bed, acquired sequentially). These can then be used to calculate the slope for the rate of change of uptake.

In another implementation the reconstruction of the derivative image is done using a regional reconstruction algorithm (such as in Schottlander et al, Quantification of Tomographic Data by Projecting Continuous Regions-of-Interest, IEEE-MIC-NSS 2006) for estimating the spatial average of the derivative signal in an entire region of interest (ROI), assuming the behavior of that ROI contains tissue of similar pathophysiological behavior.

One application of this method is to use the derivative image to detect motion of the patient during the scan. For example, if the patient moves, the uptake of tracer will suddenly vary at the edge of a high contrast area, which means that the estimated slope will be unexpectedly high in absolute value. This can be used as a quality control for the scan itself, as the variation should be much higher than values obtained from physiological tracer uptake.

To investigate the feasibility of detecting differences in the local gradient of time activity curves (TACs) over the time interval of a typical static scan, a synthetic phantom was generated with known TACs and a PET acquisition simulated using PET-SORTEO (Reilhac, A. et al. PET-SORTEO: A Monte Carlo-based simulator with high count rate capabilities. IEEE Trans. Nucl. Sci. 2004. 51(1) 46-52). The example is generated using an embodiment of the invention using generations of a number of frames per bed position, but similar results can be obtained from, for example, the direct list mode reconstruction.

Figure 6:
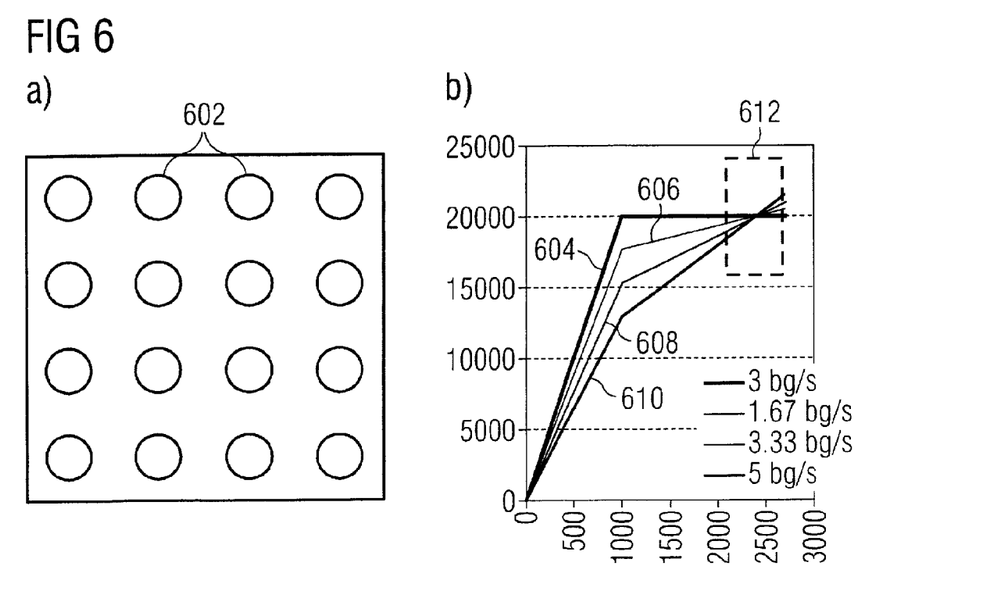

The generated phantom comprised 16, uniformly-arranged, spherical regions (602) of 32 mm diameter (FIG. 6a). Each spherical region was assigned one of four pre-calculated TACs (604, 606, 608, 610, FIG. 6b), producing four replicates of each. Over the period being simulated, each TAC had the same mean intensity, but a different gradient; specifically, 0 Bq/s (Becquerels), 1.67 Bq/s, 3.33 Bq/s and 5 Bq/s (FIG. 6b).

PET-SORTEO, a Monte Carlo simulator of realistic PET images, was used to generate a simulated sinogram of a PET acquisition of the above phantom with the associated TACs. In this example, the simulated sinogram comprised ten, 1 min frames, corresponding to the time interval from 35 mins-45 mins (dashed box 612 FIG. 6b). Each frame was reconstructed using FBP (Filtered Back Projection). The PET-SORTEO simulation and reconstruction was performed twice to produce a total of eight replicates for each TAC.

Figure 7:
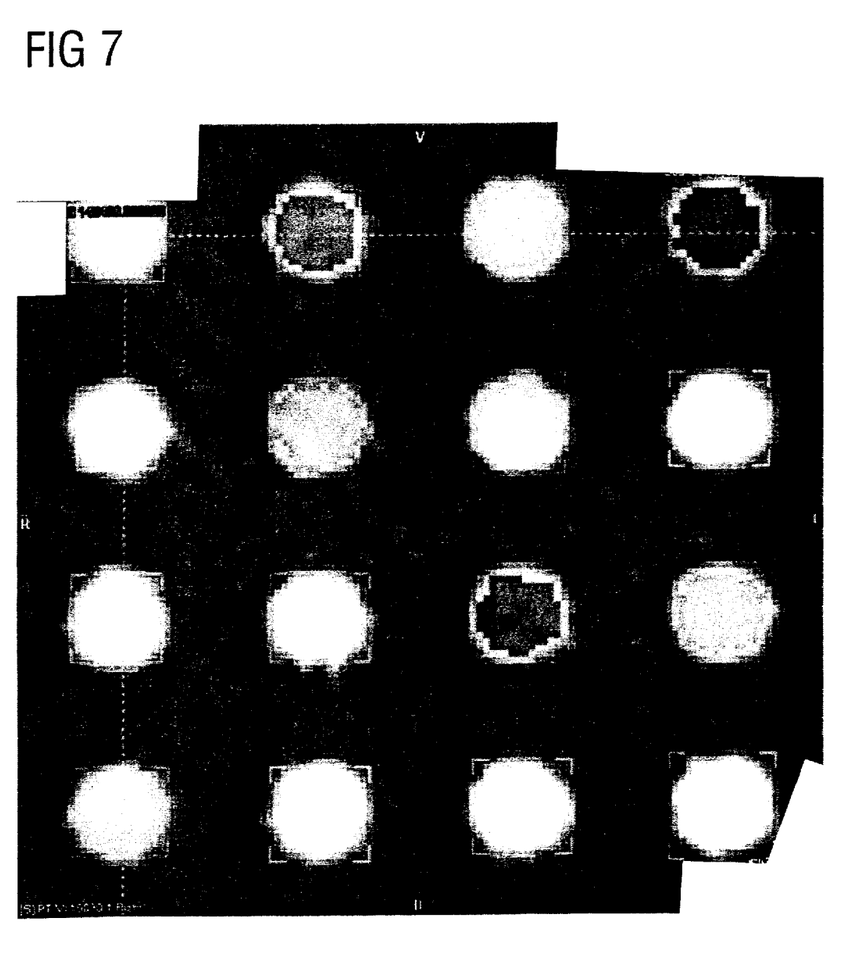
FIG. 7 is a diagram of the synthetic phantom of FIG. 6a with ROIs drawn for each spherical region.

An ROI was drawn on each spherical region by manual thresholding on the summed image (FIG. 7—a slice image of the phantom). TACs were extracted for each ROI, and the probability of distinguishing each positive-gradient TAC from the flat-gradient TAC determined for a range of scan times.

Figure 8:
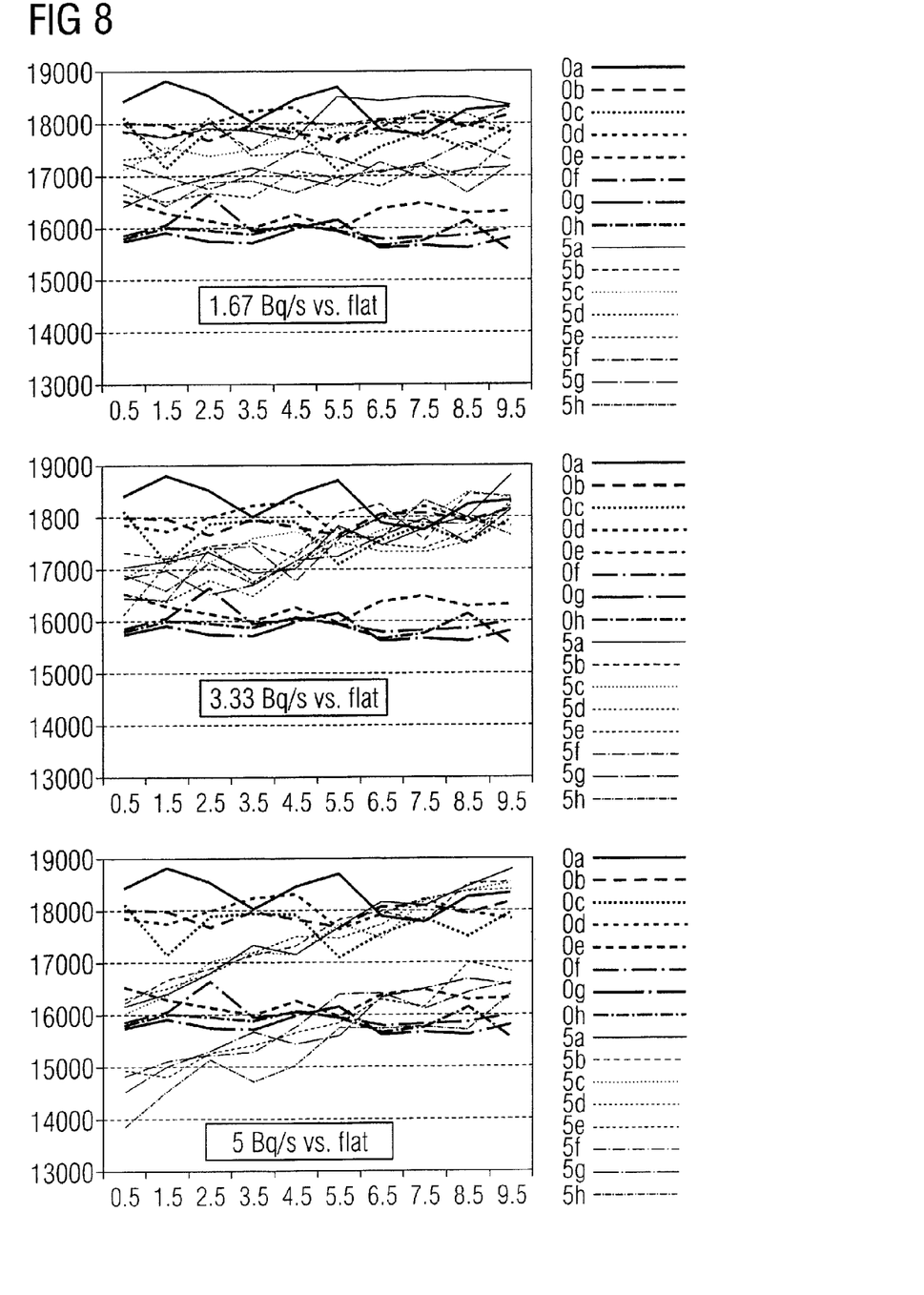
FIG. 8 is a set of graphs illustrating comparison of the TACs of FIG. 6b with the "flat" TAC of FIG. 6b.

The TACs extracted from the ROIs for the ten reconstructed 1 min frames are shown in FIG. 8, a comparison of the three positive-gradient TACs with the flat TACs extracted from the PET-SORTEO simulated dynamic image volume. In each case, the flat gradient TACs are shown in black, with the positive-gradient TACs in grey (1.67 Bq/s, 3.33 Bq/s, and 5 Bq/s). These TACs provide a visual indication of the level of noise introduced as part of the PET acquisition process.

To assess the feasibility of identifying a difference in the gradient of TACs, the probability of detecting a positive gradient in the line of best fit (LOBF) for a simulated positive-gradient TAC relative to a simulated flat TAC, was calculated as follows:

1. An LOBF was generated (using linear regression), for each simulated TAC, for the set of points corresponding to the first two minutes, the first three minutes, and so on, up to the first ten minutes. This produced nine LOBFs for each ROI, each fit through an increasing number of points (from two to ten).

2. For each of the nine LOBFs from a positive-gradient input TAC, the difference in gradient for all possible comparisons of the eight repetitions to the eight flat-TAC repetitions, was computed, producing sixty-four differences.

3. From these sixty-four differences, the mean and standard deviation of the distribution were calculated.

4. Based on the assumption that these differences are approximately normally distributed, the probability of observing a positive difference in LOBF gradient for a LOBF generated from a given number of bins simulated from an input TAC of a given gradient was calculated (Table 1).

TABLE 1

Computed probabilities of observing a positive gradient in the LOBF for three different positive-gradient input TACs (when compared to a flat input TAC), when the LOBF is fit through an increasing number of points.

| N° of 1 min bins used to generate LOBF | Probability of observing difference in LOBF gradient of >0 | | |
| --- | --- | --- | --- |
| | 1.67 Bq/ml/s input TAC | 3.33 Bq/ml/s input TAC | 5 Bq/ml/s input TAC |
| 2 | 0.4697 | 0.6212 | 0.7829 |
| 3 | 0.5993 | 0.7290 | 0.9243 |
| 4 | 0.6549 | 0.7460 | 0.9925 |
| 5 | 0.7039 | 0.7872 | 0.9989 |
| 6 | 0.9329 | 0.9879 | 1.0000 |
| 7 | 0.9802 | 0.9997 | 1.0000 |
| 8 | 0.9600 | 0.9990 | 1.0000 |
| 9 | 0.9770 | 1.0000 | 1.0000 |
| 10 | 0.9939 | 1.0000 | 1.0000 |

The results presented in Table 1 indicate that in order to achieve at least 95% confidence in detecting a deviation in input TAC gradient from flat, for 1.67 Bq/ml/s, 3.33 Bq/ml/s and 5 Bq/ml/s gradients require seven, six and four one minute bins, respectively, to construct the LOBF. This clearly demonstrates the feasibility of the method, using this particular embodiment.

A particular application for this method of deriving a slope from a static scan data period is described below.

In a PET scan, for the purpose of calculating SUV and interpreting the scan, it is the amount of radiotracer injected into the patient, alone, that is assumed to influence the supply of tracer to a tissue region at any given time. As such, SUVs from static scans are directly compared across different scans, whether they are of the same patient for tracking disease progression, or between different patients for determining entry into a trial, or patient stratification.

This assumption is flawed, however, for patients with altered kidney function, in which the rate of tracer clearance from the blood (and therefore supply to a tissue region) is either above, or below, normal. Kidney function can be impaired, for example, with age, diabetes, or following treatment with certain chemotherapeutic agents.

Through its effect on tracer concentration in the blood, alterations in kidney function can affect the measured SUV, resulting in the misinterpretation of apparent differences in tissue region uptake as being due to physiological changes in the tissue region.

Typically, potential differences in kidney function are not assessed prior to a clinical PET scan. However, for patients with known severe kidney damage or failure, the decision may be taken not to scan with a radiotracer such as 18F-FDG, since the tracer will not be cleared from the blood pool, resulting in high background activity in the scan and poor contrast.

Efforts to standardize the time between tracer administration and scan acquisition are made within clinical centers, along with measuring blood glucose concentration and fasting (for 18F-FDG scans), in an attempt to minimize the impact of uncontrolled variables on the acquired scan, but such efforts will not address the issue of differences in kidney function.

An estimate of kidney function can be made by measuring radiotracer accumulation in the bladder, since bladder accumulation is dependent on the rate of clearance of radiotracer (from the blood) by the kidneys.

From a static PET acquisition, an estimate of the total amount of radiotracer cleared from the blood pool into the bladder can be made by measuring the total activity in the bladder; however, this would required that the bladder is not emptied between tracer administration and PET acquisition. Typically, the patient is encouraged to empty his or her bladder prior to PET acquisition to aid visualization of the lower abdomen and improve patient comfort.

Figure 9:
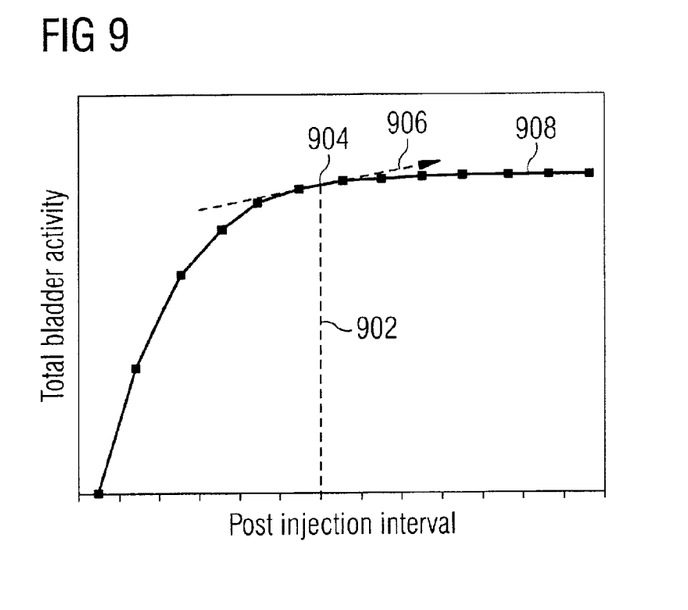
FIG. 9 is a schematic diagram illustrating a total activity curve for the bladder.

For a dynamic PET acquisition, that captured the time of radiotracer administration, and included the bladder in the FOV, both the total amount of radiotracer cleared from the blood pool into the bladder, and the rate of radiotracer clearance from the blood pool into the bladder, can be estimated for any given time point (FIG. 9). The total amount of radiotracer (904) cleared from the blood pool into the bladder at the time point indicated by the dotted line 902) corresponds to the height of that line. The rate of clearance (906) corresponds to the slope of the dashed arrow tangential to the time activity curve (908) at this time point.

The majority of clinical PET acquisitions use a static protocol, due to the ease of execution and increased throughput. Given the likelihood of bladder emptying between tracer administration and PET acquisition, an estimate of the total amount of radiotracer cleared from the blood pool into the bladder cannot be measured directly from the activity in the bladder.

However, using the methodology described above, in which the gradient of the intensity of a given region is estimated from the data acquired over the period of a typical static acquisition, the rate of radiotracer clearance from the blood pool into the bladder can be estimated.

The estimated rate of radiotracer clearance, along with the post injection interval can then be compared with a 'normal' bladder TAC in order to assess the normality of the kidney function. For example, the 'normal' bladder TAC can be derived from a series of dynamic PET acquisitions, that include the bladder in the field of view and capture radiotracer administration, from patients whose kidney function is known to be within the normal physiological range. The result is an averaged TAC of the total activity in the bladder with the measured variance in this activity at each time point. It may be necessary to scale this 'normal' TAC based on the total activity injected into the patient to compensate for large deviations in injected dose.

Figure 10:
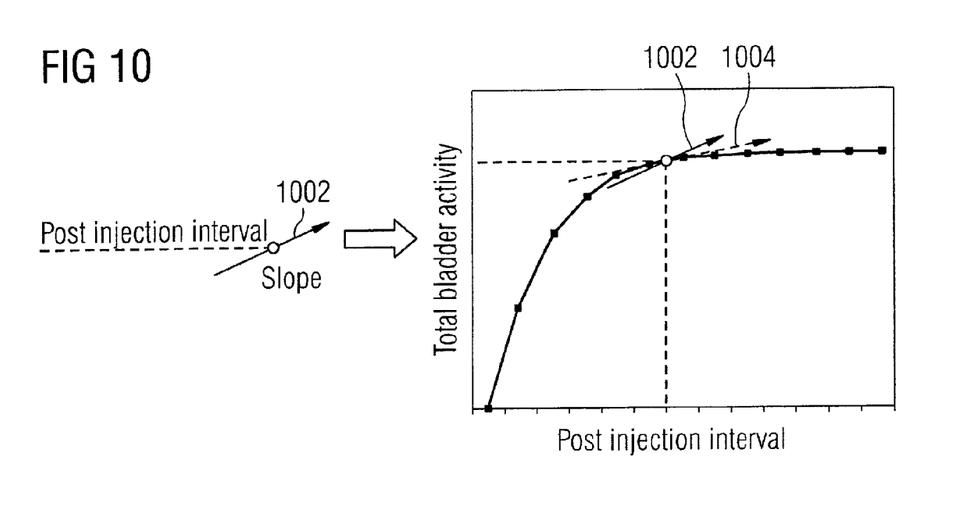
FIG. 10 is a schematic diagram illustrating a total activity curve for the bladder, and comparison with a slope for a 'normal' bladder TAC.

The rate of radiotracer clearance from the blood pool into the bladder, as estimated from an ROI corresponding to the bladder volume using the methodology described above, can then be compared to the rate (i.e., the slope) of the 'normal' bladder TAC at the same post injection interval (1002 in FIG. 10). FIG. 10 is a comparison of the rate of radiotracer clearance (1004) from the blood pool into the bladder as estimated using the derivative estimating method described above, to a normal bladder TAC slope (1002). If the rate of clearance is within the measured variance then the kidney function could be considered within the 'normal' range. However, if it is out side this range, then the clinician reading the scan is informed of a possible deviation from 'normality'.

The results of the comparison can then be used in any of the following ways:

1. Quality control (individual scan)—any significant deviations from a 'normal' range of values is flagged up to the scan reader to ensure they are aware of the altered kidney function.

2. Quality control (comparing scans)—any significant difference in clearance between the two scans is flagged up to the scan reader to ensure they are aware of the potential influence of altered kidney function on uptake values observed.

3. Correction—a revised SUV measure is computed with the intention of correcting for alterations in kidney function.

An alternative application of this method is to delay the acquisition period of the scan based on the rate of clearance into the bladder. For example, if the kidneys are clearing very slowly, the acquisition time post injection can be delayed.

As an alternative to comparison to a 'normal' bladder TAC to estimate the clearance of radiotracer from the blood into the kidneys, a function can be derived that relates both post injection interval and computed slope to clearance. This function may, for example, be derived from empirical studies of observed bladder TACs, or analytically from a model of tracer accumulation in the bladder.

This method can also be applied to other imaging modalities for which data are collected dynamically and for which the physiological behavior of the imaging agent is dependent on kidney function (e.g., SPECT).

Figure 11:
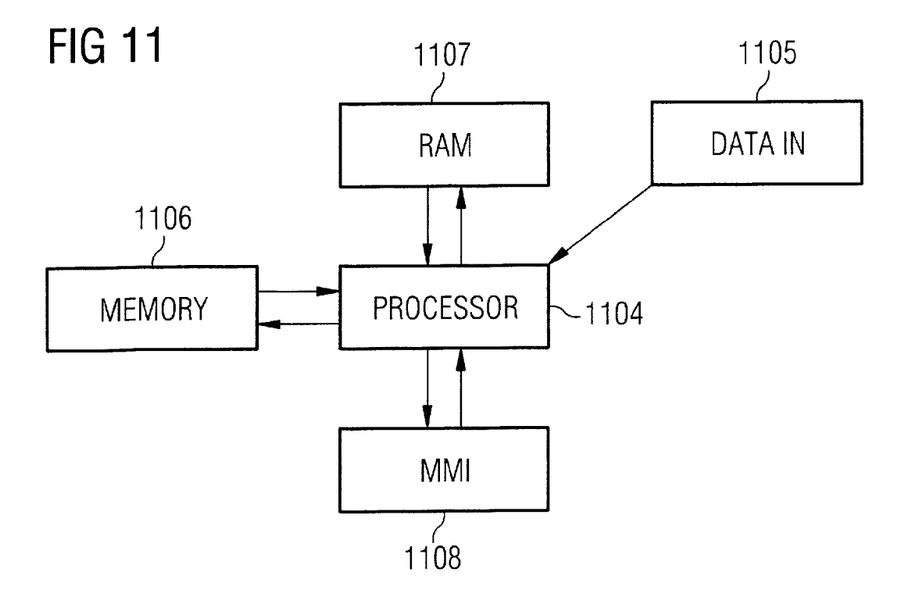
FIG. 11 is a diagram illustrating an apparatus according to an embodiment of the invention.
Figure 12:
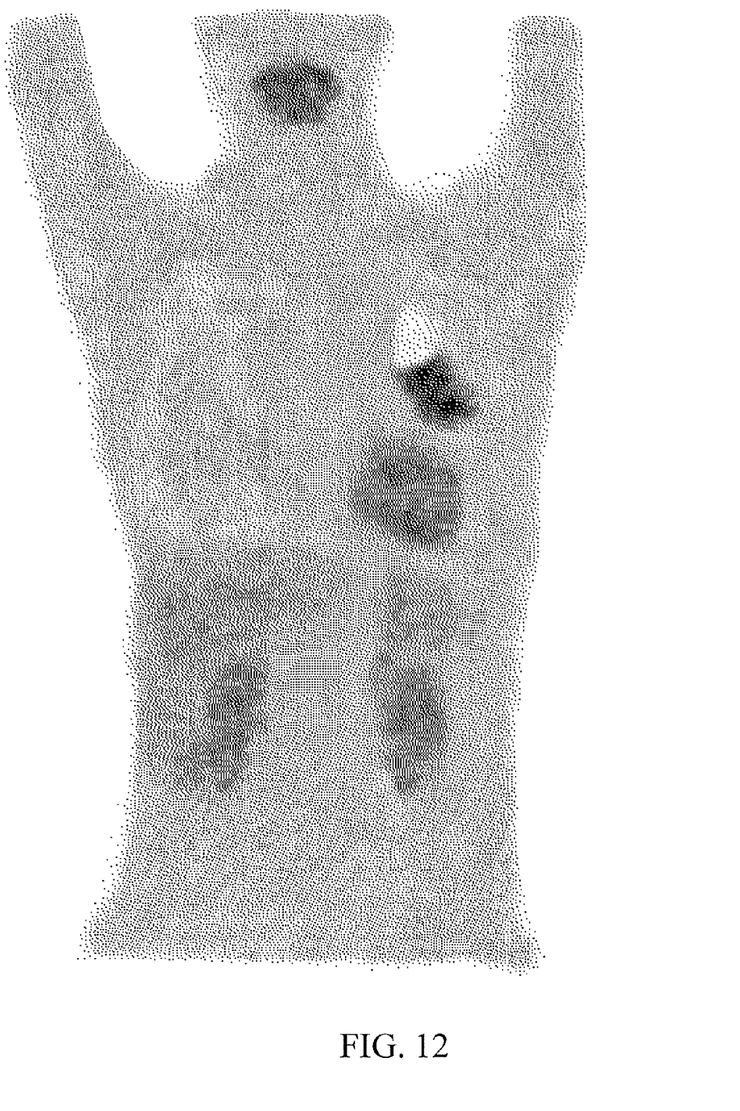
FIG. 12 illustrates a derivative image as generated and displayed in accordance with the present invention.

Referring to FIG. 11, the above embodiments of the invention may be conveniently realized as a computer system suitably programmed with instructions for carrying out the steps of the methods according to the invention.

For example, a central processing unit 1104 is able to receive data representative of medical scans via a port 1105 which could be a reader for portable data storage media (e.g. CD-ROM); a direct link with apparatus such as a medical scanner (not shown) or a connection to a network.

Software applications loaded on memory 1106 are executed to process the image data in random access memory 1107.

A Man-Machine interface 1108 typically includes a keyboard/mouse/screen combination (which allows user input such as initiation of applications) and a screen on which the results of executing the applications are displayed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of analyzing medical image data of a subject from an imaging modality using a tracer, comprising the steps of:
supplying a computerized processor with image data obtained from detection of tracer emission events in a plurality of voxels of a scanned imaging volume;
in said processor, automatically processing the image data to establish, for each of said voxels, sub-periods within a scan period for the emission events;
in said processor, calculating a rate of change of emission events per unit time for such of said voxels; and
in said processor, reconstructing a derivative image comprised of voxels each representing said calculated rate of change of emission events per unit of time for the respective voxels, and making said derivative image available in electronic form at an output of said processor in a format allowing said derivative image to be displayed.

2. A method according to claim 1, wherein the sub-periods are a plurality of divisions of the scan period, and wherein the step of processing comprises establishing a division for each emission event in the region within the scan period.

3. A method according to claim 2, wherein the step of calculating comprises:
deriving a tracer uptake value for each division by obtaining a number of emission events in each division;
fitting a line through the uptake values for the divisions; and
using the slope of the fitted line to determine the rate of change of emission events per unit time for the given region.

4. A method according to claim 1, wherein the sub-periods are time points within the scan period.

5. A method according to claim 4, wherein the step of calculating comprises fitting a line through the emission events at the associated time points, and using a slope of the fitted line to determine the rate of change of emission events per unit time for the given region.

6. A method according to claim 1, further comprising generating a first representation of the medical imaging data from the calculated rate of change of emission events per unit time for the given region.

7. A method according to claim 6, further comprising generating a second representation of data by: obtaining data from detection of tracer emission events at the least one region of a scanned imaging volume; and averaging a number of emission events across the scan period for the given region.

8. A method according to claim 1, wherein a first organ of the subject is of a type known to affect processing of the tracer in the subject, and a second organ of the subject is of a type known to accumulate the tracer as a function of an effect caused by the first organ, the method further comprising:
obtaining image data from detection of tracer emission events in a plurality of voxels of the imaging volume representing the second organ;
comparing a rate of change of emission events per unit time for each voxel with a model for the rate of change of emission events per unit time for the second organ as a function of a normal effect due to the first organ.

9. A method according to claim 8, wherein the first organ is the kidney, and the second organ is the bladder.

10. A method according to claim 1, wherein the scan period over which the medical imaging data is obtained is a period of a static scan protocol.

11. A method according to claim 1, further comprising comparing the rate of change of emission events per unit time for the given region with an expected behavior for a particular type of tissue of a scan subject.

12. Apparatus for analyzing medical image data of a subject captured by a medical imaging apparatus in an imaging modality using a tracer, comprising:

a processor having an input supplied with image data from detection of tracer emission events captured by the imaging apparatus in a plurality of voxels of a scanned imaging volume, said processor being configured to automatically process the data to establish sub-periods within a scan period for the emission events for each of said voxels, and calculate a rate of change of emission events per unit time for each of said voxels, and reconstruct a derivative image comprised of voxels each representing the calculated rate of change of emission events per unit of time for the respective voxels; and a display device in communication with said processor, said processor being configured to cause display of said derivative image at said display.

13. A non-transitory, computer-readable storage medium encoded with programming instructions, said medium being loadable into a processor and said programming instructions causing said processor to analyze medical imaging data of a subject from an imaging modality using a tracer obtained by detection of tracer emission events in a plurality of voxels of a scanned imaging volume, said programming instructions causing said processor to:

process the data to establish, for each of said voxels, sub-periods within a scan period for the emission events;

calculate a rate of change of emission events per unit time for each of said voxels, and reconstruct a derivative image comprised of voxels each representing the calculated rate of change of emission events per unit of time for the respective voxels, and make said derivative image available at an output of said processor in electronic form in a format allowing display of said derivative image.

\* \* \* \* \*